United States Patent [19]

Heckmann

[11] Patent Number: 4,904,449

[45] Date of Patent: Feb. 27, 1990

[54] COLORIMETRIC GAS MEASURING DEVICE

[75] Inventor: Johannes Heckmann, Lübeck, Fed. Rep. of Germany

[73] Assignee: Drägerwerk Aktiengesellschaft, Lübeck, Fed. Rep. of Germany

[21] Appl. No.: 167,011

[22] Filed: Mar. 11, 1988

[30] Foreign Application Priority Data

Mar. 20, 1987 [DE] Fed. Rep. of Germany ....... 3709296

[51] Int. Cl.$^4$ .............................................. G01J 1/48
[52] U.S. Cl. ...................................... 422/87; 422/58; 422/59; 436/902
[58] Field of Search .................................... 422/83–88, 422/58; 436/902

[56] References Cited

U.S. PATENT DOCUMENTS

| | | | |
|---|---|---|---|
| 3,113,842 | 12/1963 | Udall | 23/254 |
| 3,437,449 | 4/1969 | Luckey | 422/85 |
| 3,507,622 | 4/1970 | Tammelin et al. | 422/87 |
| 3,884,641 | 5/1975 | Kraffczyk et al. | 422/87 |
| 3,924,219 | 12/1975 | Braun | 338/34 |
| 4,765,962 | 8/1988 | Heim | 422/86 |

FOREIGN PATENT DOCUMENTS

| | | | |
|---|---|---|---|
| 1498909 | 4/1969 | Fed. Rep. of Germany . | |
| 543854 | 12/1974 | U.S.S.R. | 422/87 |

Primary Examiner—Barry S. Richman
Assistant Examiner—T. J. Wallen
Attorney, Agent, or Firm—Walter Ottesen

[57] ABSTRACT

The invention is directed to a colorimetric gas measuring device with an indicator path which is accessible for the gas to be detected via at least one inlet opening and which, however, is otherwise closed off with respect to the ambient. The colorimetric gas measuring device is improved so that the measuring time is extended and the sensitivity increased while at the same time providing a space-saving configuration. The gas measuring device is small and convenient to handle and can be carried on the person. For this purpose, the indicator paths are configured so as to extend in circuitous manner.

11 Claims, 2 Drawing Sheets

COLORIMETRIC GAS MEASURING DEVICE

FIELD OF THE INVENTION

The invention relates to a colorimetric gas measuring device having an indicator path which is accessible to the gas to be detected via at least one inlet; however, the indicator path is otherwise separated from the ambient.

BACKGROUND OF THE INVENTION

Such gas measuring devices are known in the form of through-flow testing tubes or also as dosimeters in the form of tubes or badges. The detection of the gas occurs by means of a coloration of an indicator layer which can be in the form of a charge placed in the elongated tube or as a coating of a badge carrier. The gas concentration or gas quantity is observed either by means of a scale placed along the length of the tube or by means of a comparison of the coloring intensity with a predetermined color standard.

Such gas measuring devices in the form of testing tubes are disclosed in U.S. Pat. 3,113,842 and as dosimeter tubes in German published patent application DE-OS 14 98 909.

The known colorimetric gas measuring devices have the disadvantage that they can be only extended to a limited length because of their elongated form and therefore cannot be utilized for making measurements of any desired duration. Also, their sensitivity cannot be increased in an unlimited manner by extending the measuring length. In the case of badge-like measuring devices for determining dosage, a scale for assuring an accurate observation or for a color intensity comparison can only be applied to locations thereon which are unsuitable.

SUMMARY OF THE INVENTION

It is an object of the invention to provide a colorimetric gas measuring device of the kind referred to above which is improved so that its measuring time can be extended and its sensitivity increased. It is a further object of the invention to provide such a gas measuring device with a configuration which is space-saving as well as small and convenient to handle so that it can be carried on the person.

It is a feature of the gas measuring device of the invention that the indicator path is configured as a circuitous path.

An important advantage of the invention is that on the one hand, the indicator path can be extended in length by a multiple of the elongated embodiment and, on the other hand, for this configuration only a very small amount of space is required. In this way, the advantages of an extended gas measuring device for long-term measurements or for obtaining a high sensitivity are combined with the advantage of a small-format badge of a dosage measuring device. The line direction of the indicator path can be intertwined in any desired varied manner without limiting the access of the gas to be detected to the colorimetric indicator.

For example, a spiral winding or a meander-like intertwinement of the indicator path is suitable. However, also screwthread-like or cylinder-like formed windings can be provided and these can be either self-supporting or can be wound on a supporting body. Glass tubes which are known in association with testing tubes can be utilized to provide an outer enclosure for the indicator path. However, also flexible plastic hoses or even indicator chambers preformed from an injection-molded part together with a supporting body can be selected.

An especially advantageous embodiment of the invention is that a circuitous path in the form of an indicator strip is applied to a carrier plate which serves as a supporting body with the indicator substance being suspended in an aqueous solution and being applied directly to the carrier plate via a mask which determines the form of the circuitous path direction. The indicator path can be in the form of a channel having a cross section corresponding to a half-shell which is placed upon the carrier plate and filled with an appropriate indicator such as impregnated silica gel. Thereafter, the channels are closed off with a cover so that no only the channel inlet or channel outlet is available as an access opening for the gas to be detected. These access openings are tightly closed during the operational readiness of the device and are opened when measurements are to be made.

The covering of the circuitous path is provided with visible markings in order to be able to determine the concentration or the collected quantity with respect to the gas to be detected. In the simplest case, the visible markings can be in the form of viewing windows in a covering which is otherwise opaque and which are arranged in such a spacing from each other that with advancing coloration of the indicator path beneath the respective viewing windows, the coloring zone appears and so provides a measure of the concentration or dosage quantity. Each of the individual viewing windows can be provided with a measurement numeral so that the measured quantity can be read off successively in step-like segments. The covering can be made of transparent material for improving the precision of observation so that the entire circuitous path is visible and the course of the coloration zone can be continuously monitored. For this purpose, a graduated measuring scale can be applied along the circuitous path so that the boundary between colored and non-colored portions of the indicator path can be read off as a measured quantity. The scale graduations can be extended radially or tangentially up to the edges of the covering to provide a convenient observation for wound circuitous paths such as those having a spiral shape.

The flow speed or diffusion speed is different with increasing length of the indicator path and this difference can be compensated for by means of a suitable shape. For example, the cross section of a tube-shaped indicator path can open up toward its end in a fluted manner or an indicator path in the form of a flat strip can have a path form which opens in a scissors-like manner. The indicator path can be provided with different quantities of an indicator substance at different zones along the path length in order to vary the detection sensitivity. For example, it is possible to provide a region of high sensitivity by reducing the indicator substance directly after the inlet for the gas to be investigated, in which region small concentrations or quantities of the gas can be detected. On the other hand, the end portion of the indicator path can be provided with an increased quantity of indicator substance in which high concentrations or quantities of the gas can be detected. In this way, a gas measuring device is provided which is suitable for investigating the lowest detectable quantities as well as also higher detectable quantities.

For the simultaneous measurement of several gases of interest, not only a single indicator channel or indicator strip of flat configuration is provided; instead, several such indicator strips or channels can be provided which are parallel to each other with each indicator strip or channel being provided with another indicator which reacts specifically to a gas to be detected. In this way, a multipurpose gas measuring device is provided in a simple and space-saving manner.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
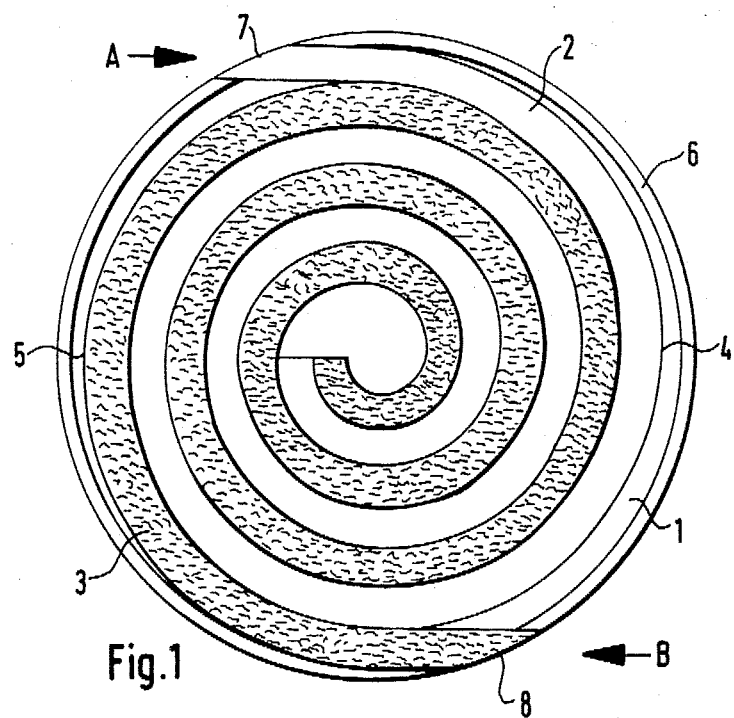
FIG. 1 is a plan view of a colorimetric gas measuring device of the invention having two spirally-formed indicator paths and shown with the cover removed.

FIG. 1 shows a gas measuring device having a circular carrier plate 1 on which a first indicator path 2 is provided for detecting a first gas A as well as a second indicator path 3 for detecting a second gas B. Both indicator paths (2, 3) are provided with different indicator substances which are specific for gases (A, B). The indicator substance for the path 3 is identified by shading.

The gas measuring device of the invention is suitable for detecting several different gases by providing the appropriate number of indicating paths and indicator substances in corresponding ones of these paths. For example, gas A could be sulphur dioxide ($SO_2$) and the corresponding indicator substance would by starch-iodine (blue color) which turns white in the presence of the sulphur dioxide. On the other hand, gas B could be any nitrous gas ($NO_2$, $NO_x$) and its indicator substance would be N, N'-diphenylbenzidine with a color change from pale gray to bluish gray in the presence of these gases. Other indicators could be used to detect other gases as delineated, for example, in the handbook entitled "Detector Tube Handbook" 6th Edition (May 1985) published by Drägerwerk AG.

The indicator paths (2, 3) are separated from each other by means of lateral partition walls (4, 5) which extend along the paths. The indicator paths (2, 3) are provided with respective inlet openings (7, 8) which extend through the wall 6 of the housing.

Figure 2:
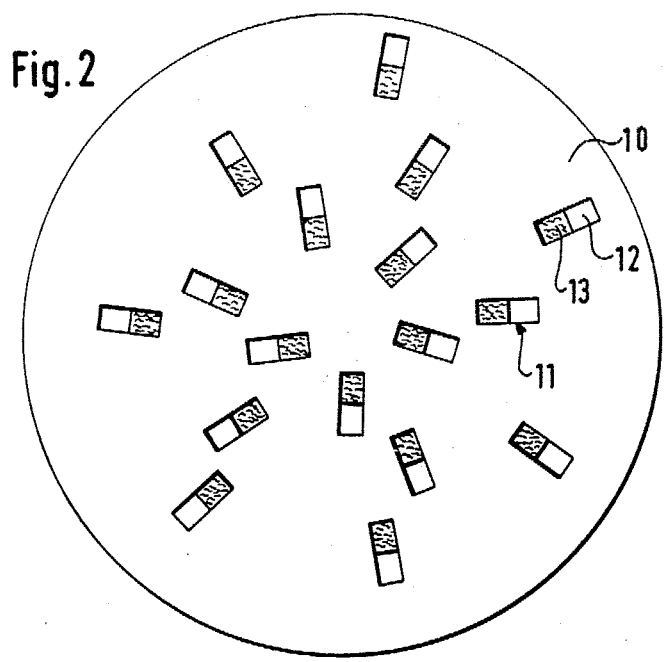
FIG. 2 is a plan view of the gas measuring device of FIG. 1 with the cover of the device shown in position over the indicator paths.

In FIG. 2, the gas measuring device is shown with a closed cover 10. Viewing windows 11 are provided and are arranged as shown in the otherwise opaque cover. The viewing windows 11 are each subdivided into component windows (12, 13) and are adapted to the spiral-like course of the indicator paths (2, 3). The viewing windows 11 are so arranged that component windows 12 are each positioned over path 2 and component windows 13 are each positioned over path 3.

The gas measuring device shown in FIGS. 1 and 2 functions as a diffusion specimen collector with the different gases (A, B) diffusing into corresponding ones of the indicator paths (2, 3) via respective inlet openings (7, 8). The gases (A, B) then migrate along respective ones of the paths (2, 3). The lateral walls (4, 5) close against the cover 10 and prevent a passing of the gas out of indicator path 2 and over to indicator path 3 and vice-versa. In this way, a coloration corresponding to the diffusion occurs in the particular indicator path (2, 3) which is noticeable through the component window (12, 13) corresponding thereto as soon as the coloration zone has reached the corresponding component window (12, 13).

By means of a separate calibration process, suitable indications of concentration can be provided at the viewing windows 11 so that when the coloration zone appears beneath a specific one of the viewing windows 11, the concentration corresponding thereto can be observed. It is noted that this calibration process must only be performed once for the specific arrangement of the indicator paths (2, 3) with respect to the corresponding viewing windows 11.

Figure 3:
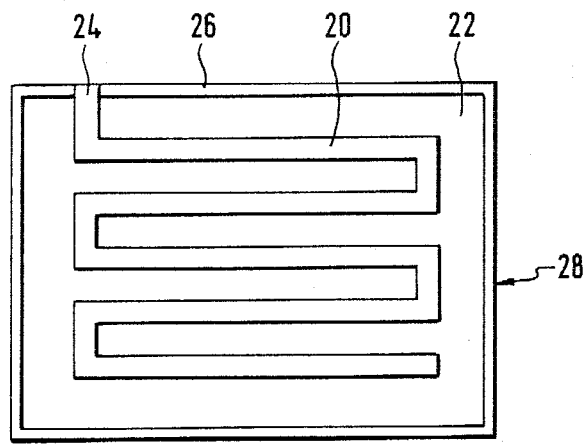
FIG. 3 shows a plan view of a gas measuring device according to another embodiment of the invention which includes a meander-like indicator path; and, FIG. 4 is a schematic representation of a gas measuring device according to still another embodiment of the invention wherein an indicator path is wound on a cylindrical body.

FIG. 3 shows another embodiment of the gas measuring device of the invention wherein an indicator path 20 is arranged on a carrier plate 22. Here, the indicator path is shown having a meander-like form. An inlet 24 extends through the wall 26 of a housing 28 which is shown with the cover removed.

Figure 4:
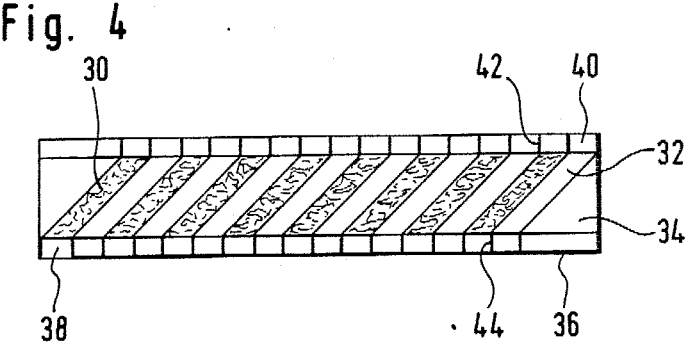

FIG. 4 shows still a further embodiment of a gas measuring device according to the invention wherein two indicator paths (30, 32) are provided on a cylindrical supporting body 34 in the manner of a winding thread. The supporting body 34 and the indicator paths (30, 32) are enclosed in a tubular glass housing 36. Separate inlets (38, 40) are provided for the indicating paths (30, 32) and walls (42, 44) extend spirally along the body 34 to prevent a gas from passing from one path to the other.

It is understood that the foregoing description is that of the preferred embodiments of the invention and that various changes and modifications may be made thereto without departing from the spirit and scope of the invention as defined in the appended claims.

What is claimed is:

1. A colorimetric measuring device for measuring a particular gas in the ambient, the device comprising:
    a housing having an inlet opening formed therein for admitting ambient gas to be detected;
    non-linear indicator path means having a predetermined non-linear length and being disposed in said housing and in gaseous communication with said inlet opening;
    said indicator path means having a constant cross section along the entire length thereof and containing an indicator extending along said non-linear length in a predetermined direction along an imaginary axis; said indicator coacting with the gas to provide a color indication of the concentration thereof;
    said indicator path means advancing in the direction of said axis by continuously crossing over said axis in the manner of a continuous waveform;
    means for permitting an observer to view said indicator path means; and,
    said housing being configured so as to isolate said indicator path means from the ambient except at said inlet opening.

2. The device of claim 1, said indicator path means comprising: a path formed in said housing; and, an indicator substance for entering into a colorimetric reaction with the gas to be measured; said indicator substance being placed in varying quantities along the length of said path.

3. The device of claim 1, wherein said measuring device is for measuring at least two different gases, said indicating path means including two paths formed in said housing and two indicating substances corresponding to respective ones of said paths for entering into a colorimetric reaction with said gases, respectively; and, said device further comprising partition means disposed between said paths for preventing a gas in one of said paths from passing over to the other one of said paths.

4. A colorimetric measuring device for measuring a particular gas in the ambient, the device comprising:
- a housing having a surface and an axis perpendicular to said surface, said housing having an inlet opening formed therein for admitting ambient gas to be detected;
- non-linear indicator path means disposed in said housing and in surrounding relationship to said axis and having a predetermined non-linear length and being in gaseous communication with said inlet opening;
- said indicator path means having a constant cross section along the entire length thereof and containing an indicator extending along said non-linear length for coacting with the gas to provide a color indication of the concentration thereof;
- said indicator path means extending spirally from said inlet opening to define a spiral about said axis;
- said housing being configured so as to isolate said indicator path means from the ambient except at said inlet opening;
- said housing having a base and said indicator path means being formed on said base;
- said housing including a cover disposed above said indicator path means; and,
- viewing means arranged at predetermined intervals along the length of said indicator path means for facilitating an observation of the latter.

5. The device of claim 4, said cover being opaque and said viewing means being a plurality of viewing windows formed in said cover, said viewing windows being arranged at predetermined intervals along the length of said indicator path means.

6. A colorimetric measuring device for measuring a particular gas in the ambient, the device comprising:
- a housing having a surface and an axis perpendicular to said surface, said housing having an inlet opening formed therein for admitting ambient gas to be detected;
- non-linear indicator path means disposed in said housing and in surrounding relationship to said axis and having a predetermined non-linear length and being in gaseous communication with said inlet opening;
- said indicator path means having a constant cross section along the entire length thereof and containing an indicator extending along said non-linear length for coacting with the gas to provide a color indication of the concentration thereof;
- said indicator path means extending spirally from said inlet opening to define a spiral about said axis;
- said housing being configured so as to isolate said indicator path means from the ambient except at said inlet opening;
- said housing having a base and said indicator path means being formed on said base;
- said housing including a cover disposed above said indicator path means; and,
- said cover being transparent and having marking means formed thereon as a plurality of graduations arranged on said cover at predetermined intervals along the length of said indicator path means.

7. A colorimetric measuring device for measuring a particular gas in the ambient, the device comprising:
- an elongated supporting body;
- non-linear indicator path means having a predetermined non-linear length and being spirally wound on said body;
- a housing having inlet means formed therein so as to be in gaseous communication with said indicator path means for admitting ambient gas into the latter;
- said housing enclosing said body and said indicator path means so as to separate the latter from the ambient except at said inlet means;
- said indicator path means having a constant cross section along the length thereof and containing an indicator extending along said non-linear length for coacting with the gas to provide a color indication of the concentration thereof; and,
- means for permitting an observer to view said indicator path means.

8. A colorimetric measuring device for measuring two gases in the ambient, the device comprising:
- a housing having a flat base defining a surface and a wall extending upwardly from said base;
- first and second indicator paths formed in said housing on the surface of said base so as to define respective non-linear path lines on said surface;
- first and second indicator substances disposed along corresponding ones of said indicator paths for entering into colorimetric reactions with two gases, respectively;
- first and second inlets formed in said wall for communicating with said indicator paths, respectively, to permit said two gases to migrate along corresponding ones of said indicator paths;
- a cover mounted on said wall so as to be above said indicator paths;
- means for permitting an observer to view said indicator path means; and,
- partition means extending between said base and said cover for separating said paths from each other along the respective lengths thereof.

9. The device of claim 8, said paths being formed as two mutually adjacent spiral paths; and, said device further comprising viewing means arranged at predetermined intervals along said indicator paths for facilitating an observation of said paths.

10. The device of claim 9, said cover being opaque and said viewing means being a plurality of viewing windows arranged at predetermined intervals along the length of said indicator paths.

11. A colorimetric measuring device for measuring a particular gas in the ambient, the device comprising:
- a housing having a surface and an axis perpendicular to said surface, said housing having an inlet opening formed therein for admitting ambient gas to be detected;
- non-linear indicator path means disposed in said housing and in surrounding relationship to said axis and having a predetermined non-linear length and being in gaseous communication with said inlet opening;

said indicator path means having a constant cross section along the entire length thereof and containing an indicator extending along said non-linear length for coacting with the gas to provide a color indication of the concentration thereof;

said indicator path means extending spirally from said inlet opening to define a spiral about said axis;

means for permitting an observer to view said indicator path means; and, said housing being configured so as to isolate said indicator path means from the ambient except at said inlet opening.

* * * * *